US00PP35779P2

(12) United States Plant Patent
Olesen

(10) Patent No.: US PP35,779 P2
(45) Date of Patent: Apr. 30, 2024

(54) MINIATURE ROSE PLANT NAMED 'Poulpah116'

(50) Latin Name: *Rosa hybrida*
Varietal Denomination: Poulpah116

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,484

(22) Filed: Sep. 8, 2023

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121, 128
CPC ..... A01H 5/0222
See application file for complete search history.

(56) References Cited

PUBLICATIONS

CPVO Application Consultation Version 4.12.8 Citation for 'Poulpah116'; Nov. 14, 2023; 2 pages.*

* cited by examiner

*Primary Examiner* — Kent L Bell

(57) ABSTRACT

A new garden rose plant of the miniature class which has abundant, pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah116'.

This application claims priority to Plant Breeder's Rights Application Number 2022/2164, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah116', originated as a single seedling from the stated cross.

The new variety may be distinguished from its male pollen parent and female seed parent primarily by the following characteristics. The male pollen parent plant has light red flowers while the new variety has pink flowers. The female seed parent plant has light red flowers while the new variety has pink flowers.

The objective of the hybridization of this rose variety was to create a new and distinct variety with unique qualities, such as:

1. Uniform and abundant pink flowers;
2. Vigorous, but compact growth when propagated on its own roots;
3. Exceptional disease resistance.

This combination of qualities is not present in previously available commercial cultivars of this type, known to the inventor, and distinguish 'Poulpah116' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah116' was selected in the spring of 2016 by the inventor as a single plant from the progeny of the aforementioned hybridization.

Asexual reproduction of 'Poulpah116' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah116' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah116'.

Specifically illustrated in FIG. 1 of the drawings are open flowers viewed from the side and above, flower petals detached, flower bud, and sepals detached revealing reproductive flower parts.

Figure 1:
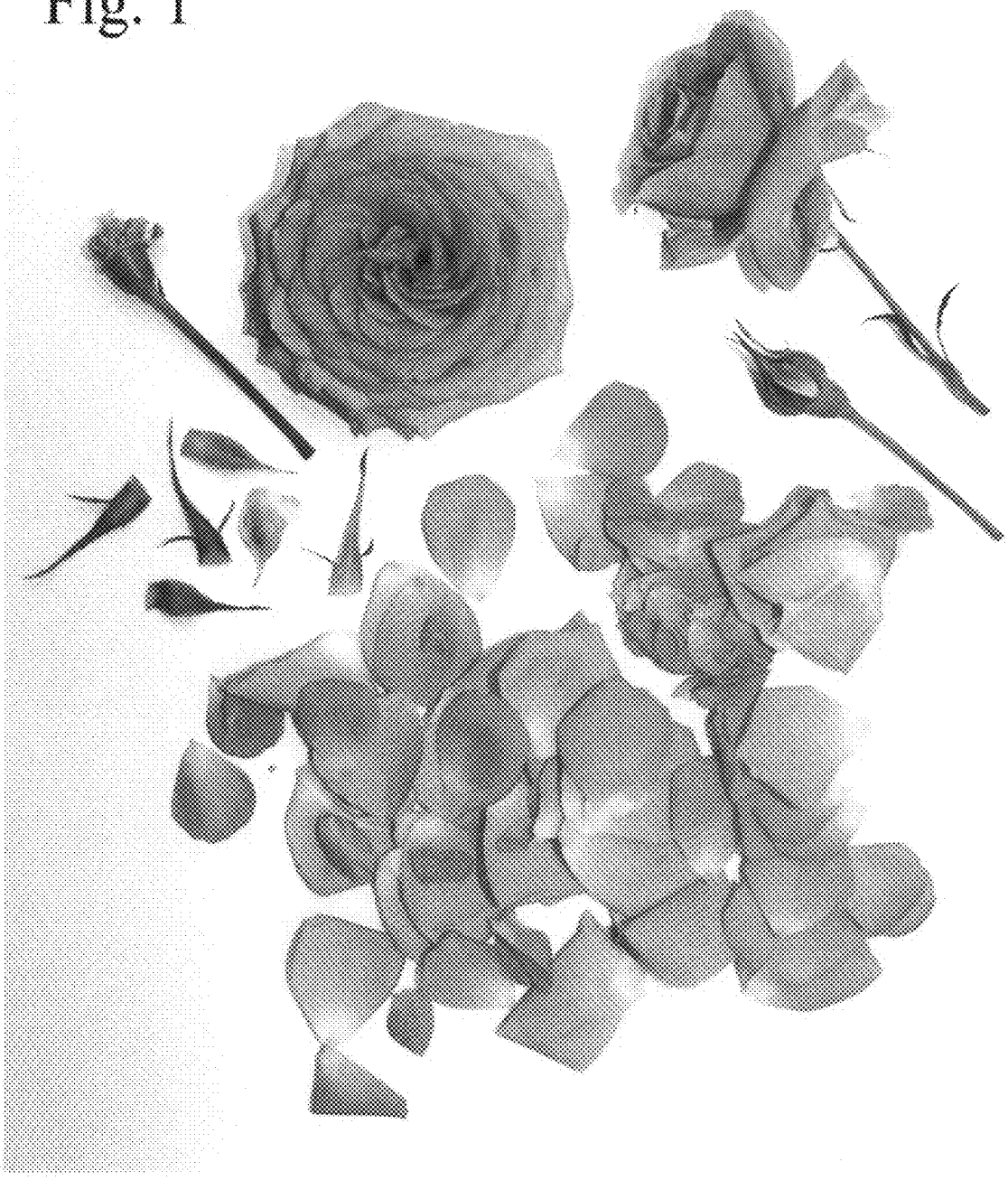
Figure 2:
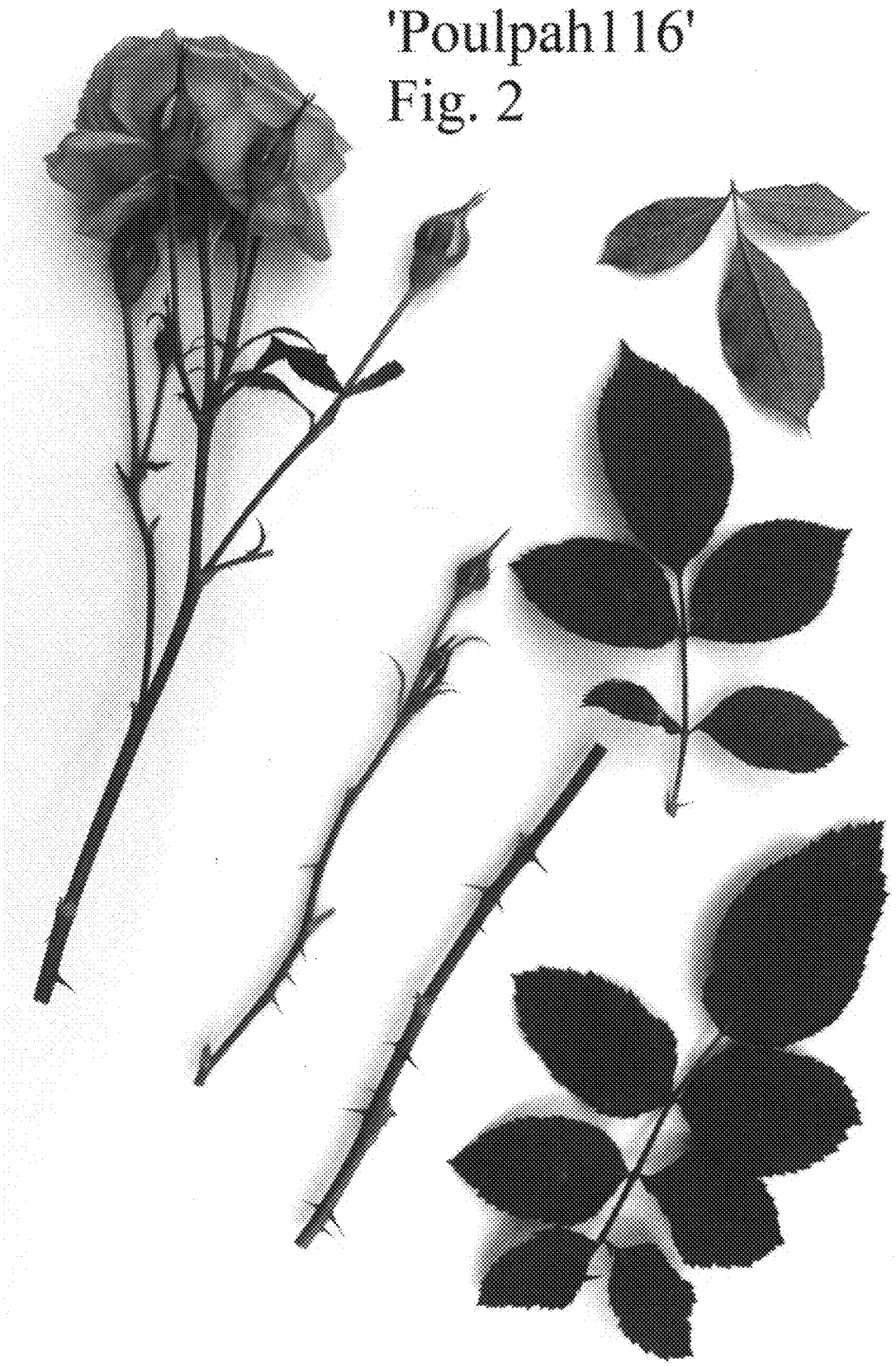

Specifically illustrated in FIG. 2 of the drawings are juvenile and mature leaves, juvenile and mature bare stems exhibiting prickles, and a cluster of flowers on the branch. Plants shown are 5 months of age.

DETAILED DESCRIPTION OF THE VARIETY

The following is a description of 'Poulpah116', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah092', U.S. Plant Pat. No. 29,725 are compared to the claimed plant. While 'Poulpah116' has 98 flower petals, 'Poulpah092' has 45 flower petals. Open flowers of 'Poulpah116' have a general tonality of Red-Purple Group N57C and Red-Purple 65A while 'Poulpah092' is Red-Purple Group 69A. Peduncles of 'Poulpah092' have strong intonations of Greyed-Purple Group 183B, while the claimed plant lacks the anthocyanin pigment, remaining Yellow-Green Group 144A.

FLOWER AND FLOWER BUD

Blooming habit: Continuous.

Flower bud:

- *Size.*—Upon opening, 23 mm in length from base of receptacle to end of bud. Bud diameter is 13 mm.
- *Bud form.*—Globose.
- *Bud color.*—As sepals divide petals are Red-Purple Group 58B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—About 35 mm long, 6 mm wide.
- *Receptacle.*—Texture: Smooth. Size: 10 mm in height, 8 mm wide. Color: Yellow-Green Group 144A. Shape: Campanulate.
- *Pedicel.*—Surface: Smooth. Length: 40 mm. Diameter: 2 mm on average. Color: Yellow-Green Group 144A. Strength: Strong.
- *Peduncle.*—Length: 2 to 3 cm. Diameter: About 3 mm. Color: Yellow-Green Group 144A. Texture: Smooth.

Flower bud development: Flower buds are borne in clusters of 5 to 9 flower buds per stem.

Flower bloom:

- *Fragrance.*—Moderate or light floral.
- *Duration.*—The blooms have a duration on the plant of approximately 21 days. Petals fall cleanly away from plant after flowers have fully matured.
- *Size.*—Flower diameter is about 66 mm when open. Flower depth is 25 mm.
- *Flower shape.*—Rosette, very double flower, with many slightly overlapping petals of different sizes.
- *Shape of flower, side view.*—The upper portion is convex to flat. The lower portion is concave.

Petalage: Under normal conditions, flowers have about 98 petals.

General tonality of flower: Open flowers are Red-Purple Group N57C and Red-Purple 65A.

Petal color:

- *Upon opening, outer petals.*—Upper surface: Red-Purple Group 68A. Lower surface: Red-Purple Group 68B.
- *Upon opening, inner petals.*—Upper surface: Red Group 52A with Yellow 5B at basal zone. Lower surface: Red Group 51A with Yellow 5B at basal zone.
- *Basal petal spots, upon opening.*—Upper surface: Moderate sized, Yellow Group 4B. Lower surface: Moderate sized, Yellow Group 4D.
- *After opening, outer petals.*—Upper surface: Red-Purple Group 73B with a petal spot of Yellow Group 8D. Lower surface: Red-Purple Group 73B, with a basal petal spot of White Group N155B.
- *After opening, inner petals.*—Upper surface: Red-Purple Group N57D with petal spot Yellow Group 8D. Lower surface: Red-Purple Group 73A with petal spot Yellow Group 8D.

Petals:

- *Petal reflex.*—Partially reflexed.
- *Margin.*—Small point at the apex, with Very light undulations.
- *Shape.*—Broad and elliptic. Apex shape: Rounded. Base shape: Acute.
- *Size.*—36 mm (l)×35 mm (w).
- *Texture.*—Smooth.
- *Thickness.*—Thin.

Petaloids:

- *Size.*—14 mm (l) by 12 mm (w).
- *Quantity.*—About 15.
- *Shape.*—Elliptical with an acute base and rounded apices.
- *Color.*—The upper side is Red Group 52A with Yellow 5B at basal zone. The lower surface is Red Group 51A with Yellow 5B at basal zone.

Reproductive flower parts:

- *Pollen.*—None observed.
- *Anthers.*—Size: 2 mm in length. Color: Greyed-Orange Group 163B. Quantity: 40 on average.
- *Filaments.*—Color: Yellow Group 13A. Length: About 4 mm.
- *Pistils.*—Length: 10 mm. Quantity: 29 on average.
- *Stigmas.*—Color: Greyed-Yellow Group 162D.
- *Styles.*—Color: Greyed-Yellow Group 162D.
- *Location of stigmas.*—Superior in location relative to the length of the filaments and the height of the anthers.
- *Hips.*—None Observed.

PLANT

Plant growth: Upright. Plants are 44 cm in height, and 40 cm wide.

Stems:

- *Color of juvenile growth.*—Yellow-Green Group 144A.
- *Color of mature growth.*—Yellow-Green Group 146A.
- *Length.*—Canes are about 20 cm from the base of the plant to the flowering portion.
- *Diameter.*—About 4 mm.
- *Internodes.*—On mature canes about 35 mm between nodes.
- *Surface texture.*—Young wood: Smooth. Older wood: Smooth.

Long prickles:

*Incidence*.—About 13 prickles per 10 cm of stem.

*Size*.—Average length of prickles on mature stems is 5 mm.

*Shape*.—Upper portion is linear. Lower portion is linear.

*Color*.—Juvenile prickles: Yellow-Green Group 144A. Mature prickles: Greyed-Red Group 180A.

Plant foliage:

*Compound leaf*.—150 mm (l)×95 (w).

*Quantity*.—2 or 3 leaves per 10 cm of stem on average.

*Leaf bearing angle to the stem*.—45 degrees.

*Color of juvenile foliage*.—Upper side: Yellow-Green Group 146A. Lower side: Yellow-Green Group 146B.

*Color of mature foliage*.—Upper side: Yellow-Green Group 147A. Lower side: Yellow-Green Group 147B.

Plant leaves and leaflets:

*Stipules*.—Size: 11 mm long, 3 mm wide. Quantity: 2 per compound leaf. Shape: Linear, slightly broad based with outward strong appendages. Margins: Finely serrated. Color: Yellow-Green Group 147A

*Petiole*.—Length: 20 mm average. Diameter: 2 mm. Upper surface color: Yellow-Green Group 144A. Lower surface color: Yellow-Green Group 144A.

*Rachis*.—Length: About 60 mm. Upper surface color: Yellow-Green Group 144A. Lower surface color: Yellow-Green Group 144A.

*Leaflet*.—Quantity: Normally 5 or 7 leaflets. Margins: Serrated. Size: Terminal leaflets are about 73 mm long, 41 mm wide. Shape: Generally elliptical. Base: Rounded. Apex: Acuminate. Texture: Smooth. Thickness: Average. Arrangement: Odd pinnate. Venation: Reticulate. Glossiness: Slightly glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah116' substantially as described and illustrated herein.

* * * * *

'Poulpah116'

'Poulpah116'